United States Patent [19]

Vanlerberghe et al.

[11] 4,224,311
[45] Sep. 23, 1980

[54] DISUBSTITUTED DERIVATIVES OF GLYCEROL AND COSMETIC COMPOSITIONS CONTAINING THE SAME AS AN OILY EXCIPIENT THEREFOR

[75] Inventors: Guy Vanlerberghe, Montjay-la-Tour; Henri Sebag, Paris, both of France

[73] Assignee: L'Oreal, Paris, France

[21] Appl. No.: 602,961

[22] Filed: Aug. 8, 1975

[30] Foreign Application Priority Data

Aug. 12, 1974 [LU] Luxembourg .................... 70719

[51] Int. Cl.² ...................... A61K 7/42; A61K 7/021; A61K 7/025; A61K 7/32; C07C 69/22
[52] U.S. Cl. ........................................ 424/59; 424/63; 424/64; 424/65; 424/170; 424/362; 424/365; 560/186
[58] Field of Search ................ C07C/43/02; 424/65, 424/341, 343; 260/484, 614, 615

[56] References Cited

U.S. PATENT DOCUMENTS

| | | | |
|---|---|---|---|
| 1,927,295 | 9/1933 | Powers .............................. | 260/484 A |
| 1,959,930 | 5/1934 | Schmidt et al. .................. | 260/615 B |
| 1,970,578 | 2/1934 | Schoeller et al. ................ | 260/615 B |
| 2,025,984 | 12/1935 | Harris ............................... | 260/484 A |
| 2,089,569 | 8/1937 | Orthner et al. .................. | 260/615 B |
| 2,173,203 | 9/1939 | Harris ............................... | 424/363 |
| 2,228,929 | 1/1941 | Reibnitz ........................... | 260/615 B X |
| 2,236,517 | 4/1941 | Cahn et al. ....................... | 260/484 X |
| 2,248,089 | 7/1941 | Katzman et al. ................. | 424/341 X |
| 2,457,139 | 12/1948 | Fife et al. ......................... | 424/343 X |
| 2,467,884 | 4/1949 | Elias ................................. | 424/343 X |
| 2,583,576 | 1/1952 | Kern et al. ....................... | 424/343 X |
| 3,592,940 | 7/1971 | Quesada ........................... | 424/64 |
| 3,856,931 | 12/1974 | Fuchs et al. ...................... | 424/64 X |
| 3,890,358 | 6/1975 | Hutchison et al. ............... | 424/64 |
| 3,947,571 | 3/1976 | Murphy et al. .................. | 424/64 |

OTHER PUBLICATIONS

(Miall) New Dictionary of Chemistry, 12/1962, p. 203.

*Primary Examiner*—Dale R. Ore
*Attorney, Agent, or Firm*—Cushman, Darby & Cushman

[57] ABSTRACT

A disubstituted derivative of glycerol has the formula

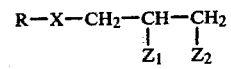

wherein one of $Z_1$ and $Z_2$ represents -YR' and the other represents hydroxy, R and R' represent a saturated and branched hydrocarbon residue of a ROH or R'OH alcohol or a R—$CO_2$H or R'$CO_2$H acid, the said alcohol or acid containing from 6-10 carbon atoms, and X and Y each independently represent oxygen or

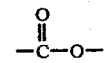

linked to R or R' through the free bond of the carbon atom of the carbonyloxy group. The said disubstituted derivative of glycerol is employed as an oily excipient in cosmetic compositions.

25 Claims, No Drawings

DISUBSTITUTED DERIVATIVES OF GLYCEROL AND COSMETIC COMPOSITIONS CONTAINING THE SAME AS AN OILY EXCIPIENT THEREFOR

The present invention relates to disubstituted derivatives of glycerol, as well as their use in cosmetic compositions.

Heretofore, certain oil derivatives of glycerol, for example, unsaturated glycerides have been proposed for various uses. However, such compounds often become rancid which prevents their practical use in cosmetic compositions.

Further, it is known that glycerides can be obtained by transesterification procedures. However, the results of such a reaction are difficultly reproducible so that the products obtained by these procedures do not always have the same or consistent characteristics.

It has now been found that certain 1,3-disubstituted derivatives of glycerol, having formula I below, do not exhibit the drawbacks of previously known oils and they can advantageously be employed principally as cosmetic oils.

The disubstituted derivatives of glycerol of the present invention are diethers, diesters or ether-esters of glycerol.

These new compounds, including those possessing a high number of carbon atoms, are liquids at ambient temperature and do not become rancid.

Further, the compounds of the present invention are advantageously employed as a cosmetic oil since they can be very easily spread onto the skin.

Additionally, the compounds of the present invention exhibit good solubilizing properties especially with perfumes, essential oils or solvents which facilitate their incorporation into cosmetic compositions.

Thus, the present invention relates to new disubstituted derivatives of glycerol, as well as mixtures of these new derivatives, having the formula

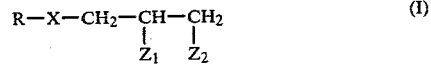

(I)

wherein one of $Z_1$ and $Z_2$ represents —YR' and the other represents a hydroxy, R and R' each independently represent saturated and branched hydrocarbon residue of a R—OH or R'—OH alcohol or a R—COOH or R'—COOH acid, the said alcohol or acid containing 6-20 carbon atoms, X and Y, each independently represent oxygen or a carbonyloxy group of the formula

which is linked to the R or R' group through the free bond of the carbon atom of said carbonyloxy group.

Preferably, the R and R' substituents are chosen so that the sum of the number of carbon atoms that they contain together is higher than or equal to 15.

Representative compounds of formula I include particularly diethers of the following formula:

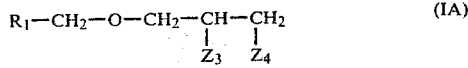

(IA)

wherein one of $Z_3$ and $Z_4$ represents —O—CH$_2$—R'$_1$ and the other represents hydroxy, R$_1$—CH$_2$— has the same definition as R given above and R'$_1$—CH$_2$— has the same definition as R' given above.

In accordance with the present invention, R and R' are principally the hydrocarbon residues of the following R—OH or R'—OH alcohols or R'—CO$_2$H or R—CO$_2$H acids, although it will be recognized that other similar types of alcohols and acids can also be employed:

(1) alcohols: 2-ethyl butanol, 2-ethyl hexanol, 2-hexyl decanol, 2-octyl decanol, octyl octanol, isostearyl alcohol and 2-octyl dodecanol; and (2) acids: 2-ethyl butyric acid, 2,2-dimethyl valeric acid, 2-ethyl hexanoic acid, 3,5,5-trimethyl hexanoic acid, neo-tridecanoic acid, isopalmitic acid and isostearic acid.

By "neo-tridecanoic acid" is meant a mixture of isomers having branched chains of tridecanoic acid.

The invention relates to a process for the preparation of compounds of formula I by the reaction of an alcohol or mixture of R'—OH alcohols, or of an acid or a mixture of R'—CO$_2$H acids on glycidyl ethers or glycidyl esters of the formula:

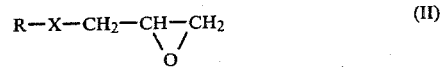

(II)

wherein R and X have the same meaning as in formula I.

The glycidyl derivatives of formula II can themselves be obtained, in the case of ethers, by treatment of the corresponding chlorohydrins in the presence of NaOH, and in the case of esters by the direct action of epichlorohydrin on the sodium or potassium salt of a R—CO$_2$H acid.

To prepare a diether of formula I (X=Y=oxygen) glycidyl ether of formula II (X=oxygen) is reacted with an alcohol or a mixture of alcohols of the formula R'—OH, in the presence of a Lewis acid catalyst, such as boron trifluoride, or in the presence of an alkaline catalyst such as sodium methylate. Generally an excess of 2 to 10 moles of R'—OH alcohol per mole of glycidyl ether of formula II is employed.

The opening of the glycidyl derivative of formula I is not unequivocal, particularly in the case where boron trifluoride is used as the catalyst, so that the reaction leads generally to a mixture of isomers. The first of such isomers corresponds to one where $Z_1$=OH and $Z_2$=—Y—R'; the second isomer corresponds to $Z_1$=—YR' and $Z_2$=—OH.

The production of the two isomers is not prejudicial to the ultimate properties of the glycerol derivative of formula I, and thus there is no real need to separate them.

The reaction leading to the formation of the diethers of formula I can be carried out without a solvent, at a temperature ranging from about 60° to 150° C., and in the presence of a catalyst disclosed above and present in a molar amount ranging from 0.2–5% relative to the glycidyl derivative of formula II.

The diesters and ether-ester of glycerol of formula I can be obtained by the action of a R'—CO$_2$H acid on a glycidyl ester or ether of formula II, in which X represents either an oxygen atom, or a

group. The reactants are used in stoichiometric proportions in the presence of a basic catalyst such as sodium methylate or triethylamine, using the same reaction conditions given above.

The present invention also relates to an oily cosmetic excipient comprising the disubstituted derivative of glycerol of formula I described above, or a mixture of said derivatives and to a cosmetic composition containing said oily cosmetic excipient.

The present invention particularly relates to the use, as a cosmetic oil, of the disubstituted derivatives of glycerol obtained in accordance with one of the processes disclosed above, and in particular to the use of the derivatives of formula I described hereafter in Examples 1-9.

It is well known that synthetic and natural oils are employed in the production of numerous cosmetic formulations. Further an examination of a vast number of cosmetic compositions reveals that practically all contain an oil, in amounts ranging from a minor proportion to a major proportion thereof.

The glycerol derivatives of formula I are liquid at ambient temperature; they have the viscosity and the unctuousness of oils; and they can be purified by molecular distillation. These disubstituted derivatives of glycerol and mixtures thereof are useful as cosmetic oils for the production of numerous cosmetic compositions, including, without being limited thereto, milks, creams, emulsions for application to the skin, various makeup products such as lip rouge and rouges, blushes, and foundations for the face, compositions for the bath and products for the protection against solar rays.

Thus, the present invention relates to cosmetic compositions containing an oily excipient comprising at least one disubstituted derivative of glycerol of formula I.

The cosmetic compositions according to the present invention are principally those wherein the said excipient is prepared in accordance with one of the processes described above and particularly to cosmetic compositions wherein the said excipient is prepared in accordance with Examples 1-9 given below.

The disubstituted derivatives of glycerol according to the present invention are generally used in the cosmetic compositions in an amount which can vary to a large degree, depending particularly on the type of cosmetic formulation in which it is present.

This amount generally ranges between 0.15 and 70 percent and preferably between 0.2 and 50 percent, by weight relative to the total weight of the composition.

The said disubstituted derivative of glycerol can be used either alone or in admixture with conventional natural or synthetic oils or even in admixture with waxes conventionally employed in cosmetic compositions.

The cosmetic compositions of the present invention can contain, in addition to the disubstituted derivatives of glycerol of formula I, conventionally employed active components or other excipients, such as surface active agents, dyes, perfumes, astringent products, ultra-violet absorbing products, preservative agents, water, alcohols and the like.

These cosmetic compositions which can be prepared in accordance with conventional procedures can comprise lip rouges, deodorants, eyelid liner or shadow formulation in stick form, creams for application to the face, hands and other parts of the human body including anti-solar creams, makeup remover creams and dye foundation creams, liquid dye foundation formulation, makeup remover milks, anti-solar milks or bath oils, etc.

The following non-limiting examples illustrate the present invention. Unless otherwise stated, all parts and percentages are by weight.

EXAMPLES OF PREPARATION

EXAMPLE 1

Preparation of the compound of formula I, wherein $X=Y=$oxygen, $R'=$2-ethyl hexyl and $R=$hydrocarbon residue of isostearyl alcohol.

To 78 g of 2-ethyl hexanol (0.6 mole) there is added 0.70 cc of $BF_3$-acetic acid complex, having 33% $BF_3$. The resulting mixture is heated to 75° C. and there are slowly added thereto 102.6 g (0.3 mole) of glycidyl isostearyl ether while maintaining the temperature at $75°\pm5°$ C. At the end of the addition, the resulting mixture is again heated for 30 minutes at 80° C. There are then added to the reaction mass with agitation, 175 cc of water at a temperature of 95° C. and containing 1.2 g of a 48% NaOH solution. Thereafter the aqueous phase is removed and the organic phase is then washed twice with 175 cc of water at 95° C.

The resulting product is dried by heating under reduced pressure and then purified by molecular distillation at 190° C. under $10^{-3}$ mm Hg. A colorless and odorless liquid is thus obtained having an end melting point lower than $-15°$ C., an Index of Refraction at 30° C. equal to 1.45082 and a viscosity of 0.29 poise at 30° C.

EXAMPLE 2

Preparation of the compound of formula I wherein $X=Y=$oxygen, $R=$2-ethyl-hexyl and $R'=$2-hexyl decyl.

To 154 g (0.6 mole) of 2-hexyl decanol, previously dried by heating under a partial vacuum, there is added 0.5 cc of a $BF_3$/acetic acid complex of 33% $BF_3$. The resulting mixture is heated to 70° C. and there are slowly added thereto 56 g (0.3 mole) of 2-ethyl hexyl ether of glycidyl while maintaining the temperature at $70°\pm5°$ C. At the termination of the addition, the mixture is again heated for 30 minutes at 80° C.

To this reaction mixture there are added with agitation, 1.5 g of a 48% NaOH solution to neutralize the catalyst. Then, with agitation 250 cc of water at 95° C. are added thereto. The aqueous phase is removed after decantation, and the remaining organic phase is washed twice with 250 cc of water at 95° C.

The reaction mass is then dried by heating under reduced pressure and excess hexadecyl alcohol is distilled off under 0.1 mm Hg.

The resulting product is purified by molecular distillation at 130° C. under $10^{-3}$ mm Hg, yielding a colorless and odorless oil, having an end liquefaction temperature lower than $-15°$ C., an Index of Refraction at 30° C. of 1.44878, and a viscosity at 30° C. of 0.31 poise.

EXAMPLE 3

Preparation of the compound of formula I wherein

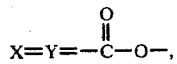

R=hydrocarbon residue of neo-tridecanoic acid and R'=hydrocarbon residue of isostearic acid.

To 19.5 g (0.061 mole) of isostearic acid, there is added 0.07 g of sodium methylate (0.0012 mole). The resulting mixture is heated under a nitrogen atmosphere to 135° C. There are then slowly added 18.4 g (0.06 mole) of glycidyl neo-tridecanoate over a 15 minute period. After 2¼ hours of heating at 135°±5° C., the amount of the reaction determined by the acid index is 98%.

Unreacted reactants are removed and the resulting product is purified by molecular distillation at 180° C. under $10^{-3}$ mm Hg, yielding a practically colorless and odorless oil, having an end melting point lower than −15° C., an Index of Refraction at 30° C. of 1.45797, and a viscosity at 30° C. of 1.5 poises.

EXAMPLE 4

Preparation of the compound of formula I, wherein X=oxygen,

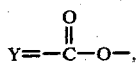

R=2-ethyl hexyl and R'=hydrocarbon residue of isostearic acid.

To 103 g (0.32 mole) of isostearic acid, there is added 0.5 g (0.009 mole) of sodium methylate. The resulting mixture is heated under a nitrogen atmosphere to 130° C., at which point there are slowly added thereto 60.4 g of 2-ethyl hexylether of glycidyl over a 35 minute period.

After 5½ hours of heating at 130° C., the amount of the reaction determined by acid index is 96%. To the reaction mass with agitation there are added 150 cc of water at a temperature of 80°-90° C., 2 g of sodium methylate in solution in methanol (5.9 meq/g) to neutralize the remaining acid and then 40 cc of isopropanol to facilitate decantation. The aqueous phase is removed and the remaining organic phase is washed twice with 150 cc of water. The reaction mass is dried by heating under reduced pressure and the product obtained is purified by molecular distillation at 192° C. under $10^{-3}$ mm Hg.

A practically colorless and odorless oil is obtained having an end temperature of liquefaction of about −15° C. and an Index of Refraction at 30° C. of 1.45152.

EXAMPLE 5

Preparation of the compound of formula I wherein X=oxygen,

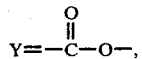

R=2-ethyl hexyl and R'=hydrocarbon residue of neo-tridecanoic acid.

To 44.5 g of neo-tridecanoic acid (0.2 mole) there is added 0.33 g of sodium methylate (0.006 mole). The resulting mixture is then heated under a nitrogen atmosphere to 130° C. 39 g of 2-ethyl hexyl ether of glycidyl (0.2 mole) are then added over a 25 minute period. After 9 hours of heating at 130° C., the amount of the reaction determined by acid index is 95%. To the reaction mass there are then added 100 cc of water at 80°-90° C., and then 1.9 g of sodium methylate in solution in methanol (5.9 meq/g) to neutralize the remaining acid. The aqueous phase is decanted and the remaining organic phase is washed twice with 100 cc of water. The reaction mass is dried by heating under reduced pressure and the product obtained is purified by molecular distillation at 135° C. under $10^{-3}$ mm Hg, yielding a practically colorless and odorless oil having an end temperature of liquefaction lower than −10° C., an Index of Refraction at 30° C. of 1.44962 and a viscosity at 30° C. of 0.52 poise.

EXAMPLE 6

Preparation of the compound of formula I wherein

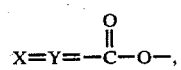

R=hydrocarbon residue of isopalmitic acid and R'=hydrocarbon residue of 2-ethyl butyric acid.

To 35 g (0.3 mole) of 2-ethyl butyric acid, there is added 0.6 g (0.006 mole) of triethylamine. The resulting mixture is heated under a nitrogen atmosphere to 135° C. and there are slowly added thereto 103 g (0.3 mole) of glycidyl isopalmitate.

After heating for 3 hours and 15 minutes at 135° C., the amount of the reaction determined by the epoxide index and acid index is close to 99%.

To the reaction mass there are added with agitation 125 ml of wqter at 80° C. containing 0.3 ml of HCl (d=1.19). After decantation the aqueous phase is separated and the remaining organic phase is washed twice with 125 ml of water at 70° C. The reaction mass is then dried under reduced pressure and the volatile products are removed by molecular distillation at 110° C.

The resulting product is distilled by the same process, at 140° C. under a pressure of $10^{-3}$ mm Hg, yielding a practically colorless oil having an end temperature of liquefaction lower than −15° C., an Index of Refraction at 30° C. of 1.44826 and a viscosity at 30° C. of 0.41 poise.

The glycidyl isopalmitate employed as an initial reactant can be prepared in the following manner:

To 512 g (2 moles) of isopalmitic acid there are added with agitation 193 g of NaOH solution of 10.3 meq/g, or 2 moles. The major part of the water is then removed by heating under reduced pressure. To the mixture there are added at 90° C., 2.940 kg of epichlorohydrin (32 moles), while continuing the removal of the remaining water. The reaction mixture is then left for 30 minutes at the reflux of epichlorohydrin which is then removed by distillation.

The reaction mass which is first washed with 750 ml of water and then twice with 400 ml of water, is then dried by heating under reduced pressure and subsequently purified by distillation; yielding a product having a boiling point of 137°-140° C. at 0.1 mm Hg.

EXAMPLE 7

Preparation of the compound of formula I, wherein X=oxygen, $$Y = -\overset{O}{\underset{\|}{C}} - O-,$$

R=2-ethyl hexyl and R'=hydrocarbon residue of 2-ethyl hexanoic acid.

To 66 g (0.45 mole) of 2-ethyl hexanoic acid there is added 0.91 g (0.009 mole) of triethylamine. The resulting mixture is heated to 135° C. under a nitrogen atmosphere. There are then slowly added thereto 84 g (0.45 mole) of 2-ethyl hexyl ether of glycidyl. After 3 hours of heating at 135° C., the amount of the reaction determined by acid index is 93%. To the reaction mixture there are added with agitation 150 ml of water at 80° C. containing 2.4 g of 48% NaOH, to neutralize the remaining acid. After decantation the aqueous phase is separated and the remaining organic phase is washed first with 150 ml of water containing 0.5 ml of HCl (d=1.19) and then with 150 ml of water at 80° C. The reaction mass is then dried by heating under reduced pressure and the resulting product is purified by molecular distillation at 87° C. under $10^{-3}$ mm Hg, yielding a colorless oil having an end liquefaction temperature lower than $-15°$ C., an Index of Refraction at 30° C. of 1.44217, and a viscosity at 30° C. of 0.17 poise.

EXAMPLE 8

Preparation of the compound of formula I wherein X=oxygen, $$Y = -\overset{O}{\underset{\|}{C}} - O-,$$

R=hydrocarbon residue of isostearyl alcohol and R'=hydrocarbon residue of 2,2-dimethyl valeric acid.

To 26 g (0.2 mole) of 2,2-dimethyl valeric acid there is added 0.4 g (0.004 mole) of triethanolamine. The resulting mixture is heated to 135° C. under a nitrogen atmosphere. 68.4 g (0.2 mole) of isostearyl ether of glycidyl are then slowly added thereto over a 20 minute period.

After heating for 2 hours and 45 minutes at 130° C., the amount of the reaction determined by acid index is 98%.

To the reaction mass there are added with agitation 100 ml of water at 80° C. containing 0.4 g of 48% NaOH. After decantation, the aqueous phase is separated and the remaining organic phase is first washed with 100 ml of water containing 0.3 ml of concentrated HCl and then twice with 100 ml of water. The reaction mass is then heated under reduced pressure and the volatile products are removed by molecular distillation at 120° C. The resulting product is then purified by distillation at 145° C. under $10^{-3}$ mm Hg, yielding a colorless oil having an end liquefaction temperature of $-15°$ C., an Index of Refraction at 30° C. of 1.45065, and a viscosity at 30° C. of 0.42 poise.

EXAMPLE 9

Preparation of the compound of formula I, wherein X=oxygen, $$Y = -\overset{O}{\underset{\|}{C}} - O-,$$

R=2-octyl dodecyl and R'=hydrocarbon residue of isostearic acid.

To 448 g (1.5 mole) of 2-octyl dodecanol there are added 1.65 ml of BF₃ acetic acid complex. To the resulting mixture there are slowly added 208.5 g (2.25 mole) of epichlorohydrin while maintaining the temperature at 75° C.±5° C. At the end of the addition the resulting mixture is heated for ½ hour at 100° C.

To the reaction mass thus obtained there are slowly added at 22° C. over a 15 minute period 225 g of a 40% NaOH solution and 480 g of tertio-butanol. The resulting mixture is heated for 45 minutes at 75° C. With vigorous agitation there are then added 150 ml of water. The reaction mass is then decanted to separate the aqueous phase and the remaining organic phase is then washed first with 150 ml of water and then with 100 ml of water.

Unreacted tertiobutanol is distilled off under reduced pressure and the resulting product is purified by distillation at 167°–177° C. under 0.1 mm Hg, yielding 2-octyl dodecyl ether of glycidyl.

To 32 g (0.1 mole) of isostearic acid there is added 0.3 ml (0.002 mole) of triethylamine. The resulting mixture is heated to 130° C. under a nitrogen atmosphere and there are slowly added thereto 40 g (0.1 mole) of 2-octyl dodecyl ether of glycidyl obtained according to the above method. After heating for 3 hours and 15 minutes at 130° C., the amount of the reaction determined by acid index is 93%.

There are then added to the reaction mass with agitation 75 ml of water at 90° C. containing 5 g of NaOH at 1.2 meq/g for neutralization of the remaining acid. After decantation, the aqueous phase is separated and the resulting organic phase is first washed with 75 ml of water at 90° C. containing 1 ml of concentrated HCl and then with 75 ml of water at 90° C.

The reaction mass is dried by heating under reduced pressure and the volatile products are removed by molecular distillation at 120° C. under $10^{-3}$ mm Hg.

The product obtained is then distilled by the same process at 230° C., yielding a yellow oil, having an Index of Refraction: $n_D^{30} = 1.45713$, a viscosity at 30° C. of 0.64 poise, and an end liquefaction temperature lower than $-15°$ C.

A—Day Cream for Dry Skin

A cream having the following composition is prepared:

| | |
|---|---|
| Product of Example 5 | 24.0 g |
| Cetyl ether polyoxyethylenated with 10 moles of ethylene oxide | 0.8 g |
| Glycerol monostearate-(self emulsifiable | 2.8 g |
| Cetyl alcohol | 1.5 g |
| Purcellin oil | 6.0 g |
| Stearic acid | 0.2 g |
| Carbopol 940 | 0.4 g |
| Triethanolamine | 0.5 g |
| Methyl para hydroxy benzoate (preservative) | 0.3 g |
| Sterile demineralized water | 63.5 g |
| | 100.0 g |

Purcellin oil is a mixture of esters of fatty acids having branched chain, sold by Dragoco. Carbopol 940 is a carboxy vinyl polymer sold by Goodrich Chemical.

A similarly effective day cream for dry skin is prepared by replacing the product of Example 5 in the above composition by the product of Example 4.

The above creams, as well as the compositions described in the following examples, are prepared according to conventional methods. Thus, for instance, the cream of this Example is prepared by heating at about 80° C., the aqueous phase containing optionally the Carbopol, the triethanolamine, etc. The fatty phase (oils, emulsifiers) are heated to the same temperature. Then the emulsion of these phases is prepared at this temperature. The resulting emulsion is then cooled to ambient temperature with agitation.

B—Lip Rouge

A lip rouge having the following composition is prepared:

| | |
|---|---|
| Ozokerite (fossile mineral wax) | 13 g |
| Ricin oil | 35 g |
| Hydrogenated lanolin | 5 g |
| Hydrogenated palm oil | 5 g |
| Oleyl alcohol | 5 g |
| Product of Example 1 | 21.75 g |
| Isopropyl lanolate | 10 g |
| Liquid lanolin | 5 g |
| B.H.T. (2,6-di-tert-butyl-p-cresol) | 0.1 g |
| Methyl parahydroxy benzoate | 0.15 g |
| | 100.0 g |
| In addition: | |
| Dye | |
| Titanium oxide | q.s.p. according to the color desired |
| Nacreous agents | |

C—Dye Foundation Cream

A dye foundation cream having the following composition is prepared:

| | | |
|---|---|---|
| Polyethylene glycol stearate | oil | 0.9 g |
| Glycerol stearate | | 5 g |
| Petrolatum oil | | 8 g |
| Product of Example 4 | | 13 g |
| Isopropyl lanolate | | 6 g |
| Cetyl alcohol | | 2.2 g |
| Methyl para hydroxy benzoate | | 0.3 g |
| Demineralized water, q.s.p. | | 100 g |
| In addition: | | |
| Titanium oxide | | |
| Kaolin | | q.s.p. for tint desired |
| Iron oxide | | |

D—Dye Foundation Cream

A dye foundation cream having the following composition is prepared:

| | |
|---|---|
| Beeswax | 9 g |
| Cetyl alcohol | 1 g |
| Diethanolamine cetyl phosphate | 0.5 g |
| Petrolatum oil | 10 g |
| Product of Example 2 | 18 g |
| Borax | 0.8 g |
| Methyl para hydroxy benzoate | 0.3 g |
| Demineralized water, q.s.p. | 100 g |
| In addition: | |
| Titanium oxide | |
| Kaolin and | q.s. according to tint desired |
| Iron oxides | |

E—Eyelid Shadow Stick

An eyelid shadow in stick form having the following composition is prepared:

| | |
|---|---|
| Ozokerite | 35 g |
| Petrolatum | 6 g |
| Lanolin | 12 g |
| Product of Example 5 | 46.95 g |
| B.H.T. | 0.05 g |
| | 100 g |

F—Cheek Rouge

A cheek rouge having the following composition is prepared:

| | |
|---|---|
| Isopropyl stearate | 29 g |
| Product of Example 4 | 34 g |
| Glycerol monostearate | 30 g |
| Kaolin | 2 g |
| Titanium dioxide | 3.5 g |
| Iron oxide | 1.5 g |
| | 100 g |

G—Skin Treating Cream

A cream having the following composition is prepared:

| | |
|---|---|
| Stearyl ether polyoxyethylenated with 10 moles of ethylene oxide | 4.0 g |
| Cetyl alcohol | 1.0 g |
| Stearyl alcohol | 1.0 g |
| Product of Example 7 | 3.0 g |
| Petrolatum | 10.0 g |
| Beeswax | 3.0 g |
| Lanolin | 3.0 g |
| Isopropyl palmitate | 5.0 g |
| Methyl para hydroxy benzoate | 0.3 g |
| Sterile demineralized water | |
| water, q.s.p. | 100 g |

A similarly effective skin treating cream is prepared by replacing the product of Example 7 in the above composition by the product of Example 8.

What is claimed is:

1. In a cosmetic composition containing an oily excipient the improvement comprising as the oily excipient an effective amount of at least one disubstituted derivative of glycerol having the formula

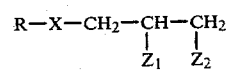

wherein one of $Z_1$ and $Z_2$ represents $-YR'$ and the other represents hydroxy, R and R' represent a saturated and branched hydrocarbon residue of a R—OH or R'OH alcohol or a R—CO$_2$H or R'CO$_2$H acid, the said alcohol or acid containing from 6 to 20 carbon atoms, and X and Y, each independently represent oxygen or

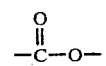

linked to R or R' through the free bond of the carbon atom of the carbonyloxy group.

2. The composition of claim 1 wherein the sum of the number of carbon atoms in R and R' is greater than or equal to 15.

3. The composition of claim 1 wherein at least one of R and R' represents the hydrocarbon residue of a R—OH or R'—OH alcohol selected from the group consisting of 2-ethyl butanol, 2-ethyl hexanol, 2-hexyl decanol, 2-octyl decanol, octyl octanol, isostearyl alcohol and 2-octyl dodecanol.

4. The composition of claim 1 wherein at least one of R and R' represents the hydrocarbon residue of a R—CO₂H or R'—CO₂H acid selected from the group consisting of 2-ethyl butyric acid, 2,2-dimethyl valeric acid, 2-ethyl hexanoic acid, 3,5,5-trimethyl hexanoic acid, neo-tridecanoic acid, isopalmitic acid and isostearic acid.

5. In a cosmetic composition containing an oily excipient the improvement comprising as the oily excipient an effective amount of at least one disubstituted derivative of glycerol having the formula

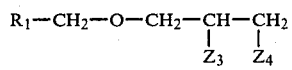

wherein one of $Z_3$ or $Z_4$ represents —O—CH₂—R'₁ and the other represents hydroxy, R₁—CH₂— has the same meaning as R given in claim 1, and R'₁—CH₂— has the same meaning as R' given in claim 1.

6. The composition of claim 1 wherein X and Y represent oxygen, R represents isostearyl and R' represents the hydrocarbon residue of 2-ethyl hexanol.

7. The composition of claim 1 wherein X and Y represent oxygen, R represents 2-ethyl hexyl and R' represents 2-hexyl decyl.

8. The composition of claim 1 wherein X and Y represent

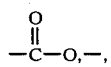

R represents the hydrocarbon residue of neo-tridecanoic acid and R' represents the hydrocarbon residue of isostearic acid.

9. The composition of claim 1 wherein X represents oxygen, Y represents

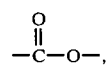

R represents 2-ethyl hexyl and R' represents the hydrocarbon residue of isostearic acid.

10. The composition of claim 1 wherein X represents oxygen, Y represents

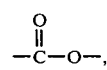

R represents 2-ethyl hexyl and R' represents the hydrocarbon residue of neo-tridecanoic acid.

11. The composition of claim 1 wherein X and Y represent

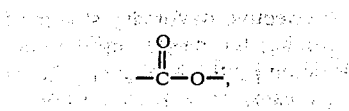

R represents the hydrocarbon residue of isopalmitic acid and R' represents the hydrocarbon residue of 2-ethyl butyric acid.

12. The composition of claim 1 wherein X represents oxygen, Y represents

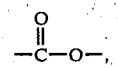

R represents 2-ethyl hexyl and R' represents the hydrocarbon residue of 2-ethyl hexanoic acid.

13. The composition of claim 1 wherein X represents oxygen, Y represents

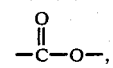

R represents the hydrocarbon residue of isostearic acid and R' represents the hydrocarbon residue of 2,2-dimethyl valeric acid.

14. The composition of claim 1 wherein X represents oxygen, Y represents

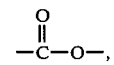

R represents 2-octyl dodecyl and R' represents the hydrocarbon residue of isostearic acid.

15. The composition of claim 1 wherein said oily excipient is present in an amount ranging between 0.15 and 70 percent by weight of said composition.

16. The composition of claim 15 wherein said oily excipient is present in an amount ranging between 0.2 and 50 percent by weight of said composition.

17. Disubstituted derivative of glycerol having the formula

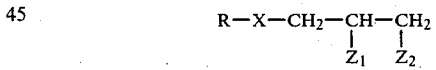

wherein one of $Z_1$ or $Z_2$ represents —YR' and the other represents hydroxy, R represents a saturated and branched hydrocarbon residue of a R—OH alcohol or a R—CO₂H acid, R' represents a saturated and branched hydrocarbon residue of a R'—CO₂H acid, the said alcohol or acid containing 6 to 20 carbon atoms, X represents oxygen or

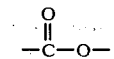

linked to R through the free bond of the carbon atom of the carbonyloxy group and Y represents

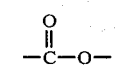

linked to R' through the free bond of the carbon atom of the carbonyloxy group.

18. The disubstituted derivative of claim 17 wherein the sum of the number of carbon atoms of R and R' is greater than or equal to 15.

19. The disubstituted derivative of claim 17 wherein X and Y represent

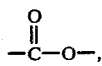

R represents the hydrocarbon residue of neo-tridecanoic acid and R' represents the hydrocarbon residue of isostearic acid.

20. The disubstituted derivative of claim 17 wherein X represents oxygen, Y represents

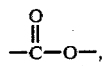

R represents 2-ethyl hexyl and R' represents the hydrocarbon residue of isostearic acid.

21. The disubstituted derivative of claim 17 wherein X represents oxygen, Y represents

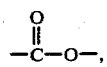

R represents 2-ethyl hexyl and R' represents the hydrocarbon residue of neo-tridecanoic acid.

22. The disubstituted derivative of claim 17 wherein X and Y represent

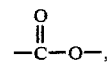

R represents the hydrocarbon residue of isopalmitic acid and R' represents the hydrocarbon residue of 2-ethyl butyric acid.

23. The disubstituted derivative of claim 17 wherein X represents oxygen, Y represents

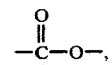

R represents 2-ethyl hexyl and R' represents the hydrocarbon residue of 2-ethyl hexanoic acid.

24. The disubstituted derivative of claim 17 wherein X represents oxygen, Y represents

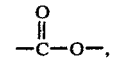

R represents the hydrocarbon residue of isostearic acid and R' represents the hydrocarbon residue of 2,2-dimethyl valeric acid.

25. The disubstituted derivative of claim 17 wherein X represents oxygen, Y represents

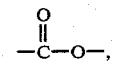

R represents 2-octyl dodecyl and R' represents the hydrocarbon residue of isostearic acid.

* * * * *